United States Patent
Quan et al.

(10) Patent No.: US 8,167,852 B2
(45) Date of Patent: May 1, 2012

(54) MICRONEEDLE DEVICE AND METHOD FOR PRODUCING THE SAME

(75) Inventors: Ying-shu Quan, Kyoto (JP); Fumio Kamiyama, Kyoto (JP); Yoshikazu Tobinaga, Otsu (JP); Tomoya Kitagawa, Otsu (JP); Kentaro Ohshima, Wakayama (JP); Akira Yamamoto, Kyoto (JP)

(73) Assignee: Cosmed Pharmaceutical Co., Ltd., Kyoto (JP)

( * ) Notice: Subject to any disclaimer, the term of this patent is extended or adjusted under 35 U.S.C. 154(b) by 0 days.

(21) Appl. No.: 12/599,860

(22) PCT Filed: Apr. 1, 2008

(86) PCT No.: PCT/JP2008/056471
§ 371 (c)(1),
(2), (4) Date: Nov. 12, 2009

(87) PCT Pub. No.: WO2008/139786
PCT Pub. Date: Nov. 20, 2008

(65) Prior Publication Data
US 2010/0228203 A1   Sep. 9, 2010

(30) Foreign Application Priority Data
May 15, 2007 (JP) ................. 2007-155752

(51) Int. Cl.
*A61M 5/32* (2006.01)
*A61M 35/00* (2006.01)
*A61K 9/02* (2006.01)

(52) U.S. Cl. ........ 604/272; 604/265; 604/274; 604/288; 604/289

(58) Field of Classification Search ...... 83/27; 604/265, 604/272, 274, 289, 288
See application file for complete search history.

(56) References Cited

U.S. PATENT DOCUMENTS

| | | |
|---|---|---|
| 2004/0096455 A1 | 5/2004 | Maa et al. |
| 2004/0265365 A1 | 12/2004 | Daddona et al. |
| 2006/0127465 A1 | 6/2006 | Maenosono et al. |
| 2008/0262444 A1* | 10/2008 | Takada .................. 604/288 |

FOREIGN PATENT DOCUMENTS

| | | |
|---|---|---|
| EP | 1 844 763 A1 | 10/2007 |
| JP | 2003-238347 A | 8/2003 |
| JP | 2005-021678 A | 1/2005 |
| US | WO2005004729 * | 1/2005 |
| WO | WO-2004/105729 A2 | 12/2004 |
| WO | WO-2005/004729 A1 | 1/2005 |
| WO | WO-2006/080508 A1 | 8/2006 |

OTHER PUBLICATIONS

International Preliminary Report on Patentability for Application No. PCT/JP2008/056471 mailed Dec. 3, 2009.
International Search Report for the Application No. PCT/JP2008/056471 mailed Jun. 17, 2008.

* cited by examiner

*Primary Examiner* — Jackie Ho
*Assistant Examiner* — Bradley Thomas, Jr.
(74) *Attorney, Agent, or Firm* — Cheng Law Group, PLLC

(57) ABSTRACT

Microneedle device is provided, which include microneedles that can be easily inserted into skin and dissolve or swell in skin. The microneedle devices comprise a substrate and cone-shaped or pyramid-shaped microneedles for skin insertion set on the substrate. The microneedles for skin insertion contain over 50 weight percent of one or multiple biomaterials chosen from chitosan, collagen, gelatin, hyaluronic acid, and they are fabricated from the materials that can dissolve or swell in the body.

4 Claims, 1 Drawing Sheet

[Figure 1]
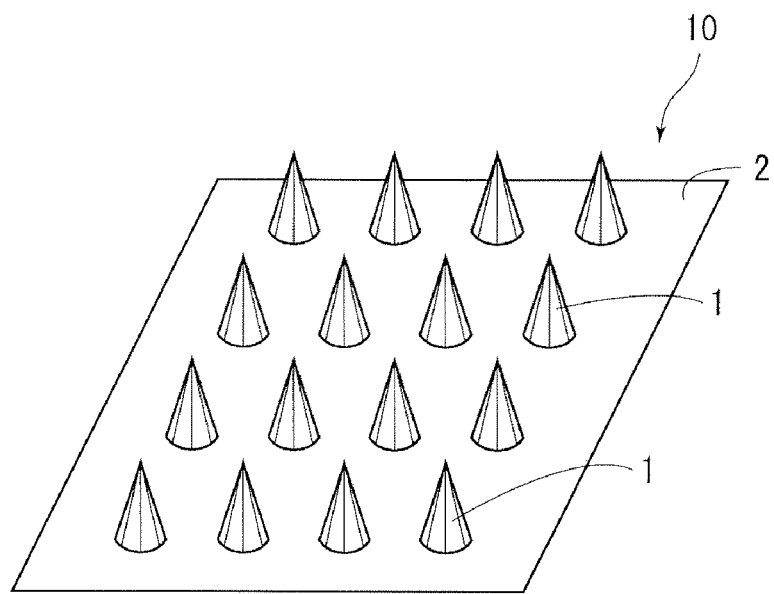
[Figure 2]
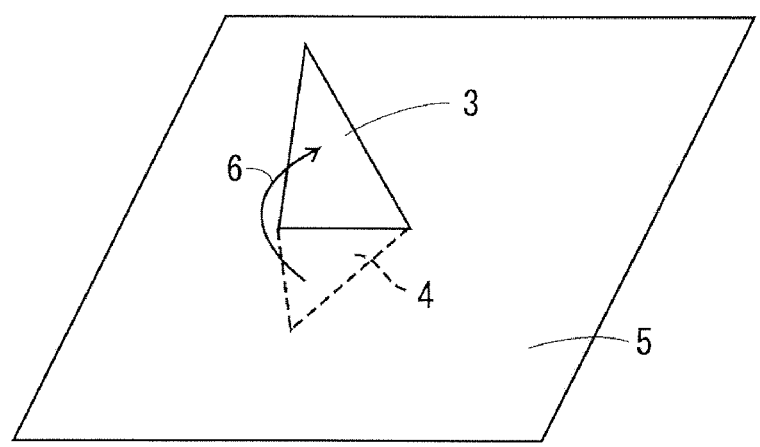

MICRONEEDLE DEVICE AND METHOD FOR PRODUCING THE SAME

FIELD OF THE PRESENT INVENTION

This invention is related to microneedle devices having microneedles for insertion into skin and methods of manufacturing of microneedle devices.

BACKGROUND OF THE INVENTION

It is well known that in order to provide decorating and/or functional effect pharmaceutical formulations such as solutions, ointments, creams, tapes, patches are commonly administered.

These formulations should be applied to the skin. Thus, they are readily lost or removed under various conditions, such as perspiration, washing and external pressure. Further, they need the permeation of pharmaceutical agents into skin and diffusion to the body in order to obtain therapeutic effects. However, it is difficult to deliver sufficient pharmaceutical agents that can get therapeutic effects due to the barrier properties of skin which prohibits the entrance of foreign materials. Moreover, it is also difficult to actually deliver pharmaceutical agents to a desired site of skin.

Iontophoresis and ultrasound have been used in an attempt of transdermal delivery of cosmetics in the field of cosmetology. However, as mentioned above, it is difficult to deliver sufficient cosmetics across the skin due to the barrier properties which prohibits the entrance of foreign materials.

Recently, to solve these problems, microneedles fabricated of metal or plastic coated with pharmaceutical agents or cosmetic agents on their surface have been used as an approach to actually deliver pharmaceutical agents to a desired site of skin. However, With this approach, however, a small quantity of pharmaceutical agents or cosmetic agents can be administrated, and the accident that microneedles made of metal or plastic left in the body often happened. Thus, they are not suitable to be applied to human.

In order to overcome these defects, many studies have been made to design microneedle devices having water-soluble microneedles. For example, Patent 1 discloses a functional microneedle that has cubical or cylindrical needles of 0.5 to 500 μm in length on the substrate. And the needle is made of saccharide such as maltose which can dissolve and disappear in the body. The cross-section of the needle is square or round with a side or diameter of 0.1 to 100 μm, respectively.
[Patent] Japanese Patent No. 2003-238347

SUMMARY OF THE INVENTION

When the above functional microneedle is inserted into skin, pharmaceutical agents are delivered to the skin with dissolution, swelling or breaking off of the needle in skin. Thus, it is possible to actually deliver pharmaceutical agents to a desired site of skin with the functional microneedle. As the needle is very sharp, there is no pain or bleeding caused by the insertion of needle into skin, and further, the closure of the pores is rapid. Therefore, the functional microneedle is suitable to actually deliver pharmaceutical agents to a desired site of skin.

If the needle is lack in mechanical strength, it would be broken during the insertion and unable to be inserted into skin. Thus, the needle preferably has sufficient mechanical strength. However, it is difficult to fabricate the needle with suitable mechanical strength by the use of saccharide such as maltose that can dissolve and disappear in the body. Moreover, maltose has a disadvantage of poor practicability due to its high hydroscopicity.

The purpose of the present invention is to provide a microneedle device which can be easily inserted into skin, leave contained pharmaceutical agents into skin by dissolution, swell or break off of needles, and dissolve or disappear in skin. It is another object of the present invention to provide a microneedle device for the administration of soluble pharmaceutical agents and cosmetic agents or at least one of them to skin.

The present invention provides a microneedle device which comprises a substrate and cone-shaped or pyramid-shaped microneedles for skin insertion fixed on the substrate. The above microneedles are characterized by their composition of biomaterials chosen from chitosan, collagen, gelatin, hyaluronic acid of 50 weight percents or more, and by their properties of dissolving or swelling in the body.

BRIEF DESCRIPTION OF THE DRAWINGS

FIG. 1 is a schematical view of the microneedle device.
FIG. 2 is a schematical view of the method of manufacturing of the microneedle device.

DESCRIPTION OF THE SYMBOLS

1, 3 Microneedles for skin insertion.
2, 3, 5 Substrates.
4 V-shaped part.
10 Microneedle device.

DETAILED DESCRIPTION OF THE INVENTION

The microneedle device of the present invention comprises a substrate and cone-shaped or pyramid-shaped microneedles for skin insertion on the substrate. These microneedles are characterized by containing over 50 weight percent of one or multiple biomaterials chosen from chitosan, collagen, gelatin, hyaluronic acid and by dissolving or swelling in the body.

In one form of the invention, the microneedles for skin insertion are characterized by containing over 50 weight percent of one or multiple biomaterials chosen from chitosan, collagen, gelatin.

Chitosan used in the present invention, for example, is a kind of polysaccharides which is the polymer of 1, 4 polymerized glucosamine. Chitosan used in the present invention is generally produced by deacetylation of chitin that obtained from the exoskeleton of crustaceans (crabs, shrimp, etc.) by some treatments such as boiling.

Gelatin used in the present invention, for example, is produced by the purification of protein that composes the connective tissue of skin, bones, cartilages, ligaments, tendons of animals. Collagen, for example, is produced by hydrolysis and further purification of above protein.

Materials such as chitosan, collagen and gelatin can be used alone or together.

In one form of the invention, the microneedles for skin insertion contain over 50 weight percents of biomaterials chosen from chitosan, collagen, gelatin, and they are characterized by materials that can dissolve or swell in the body. So far as the microneedles for skin insertion are defined to contain over 50 weight percent of above mentioned biomaterials, biomaterials other than above mentioned biomaterials of less than 50 weight percent of can be used.

Besides chitosan, collagen and gelatin, as a material which can dissolve or swell in the body, there are polysaccharides such as maltose, alginate and agarose, cellulose such as carboxymethylcellulose and hydroxypropylcellulose, starch.

In one form of the invention, the microneedles for skin insertion are characterized by containing over 50 weight percent of hyaluronic acid.

Hyaluronic acid used in the present invention is a kind of glycosaminoglycan. Hyaluronic acid is composed of the repeating disaccharide unit of N-acetylglucosamine and glucuronic acid. Glycosaminoglycan is also called mucopolysaccharide. It is preferable to use the hyaluronic acid that obtained from organism such as crista galli and umbilical cord and that obtained with the with cultivation of lactic acid bacteria, streptococcus.

The microneedle product from hyaluronic acid becomes harder as the weight average molecular weight of hyaluronic acid is smaller. And its mechanical strength increases with the weight average molecular weight of hyaluronic acid. Thus, when the weight average molecular weight of hyaluronic acid as raw material is smaller, the microneedles for skin insertion become harder and it is easy to insert them into skin, while their mechanical strength decrease and the needles are easily broken during storage and insertion. For this reason, it is preferable to use the hyaluronic acid with the weight average molecular weight larger than 400,000. The weight average molecular weight is determined by the method of gel permeation chromatography.

In one form of the invention, the microneedles for skin insertion contain over 50 weight percent of hyaluronic acid and they are can be dissolve or swell in the body. So far as the microneedles for skin insertion contain over 50 weight percent of mentioned biomaterials, other biomaterials of less than 50 weight percent which can dissolve or swell in the body can be used. Hyaluronic acid has the cosmetic result of bulging skin. Thus, it is preferred to only use hyaluronic acid to fabricate the microneedles for skin insertion.

Besides hyaluronic acid, as a material which can dissolve or swell in the body, for example, there are polysaccharides such as maltose, alginate and agarose, cellulose derivatives such as carboxymethylcellulose and hydroxypropylcellulose, starch.

In one form of the invention, the microneedles for skin insertion are characterized by containing 50 to 70 weight percent of collagen and 50 to 30 weight percent of hyaluronic acid.

The microneedles for skin insertion which contain 50 to 70 weight percent of collagen and 50 to 30 weight percent of hyaluronic acid, which are dissolvable and swellable in the body, have suitable mechanical strength and is easy to be inserted into skin and have good solubility in the skin. Thus, it is preferred that the microneedles for skin insertion is composed of biomaterials of 50 to 70 weight percent of collagen and 50 to 30 weight percent of hyaluronic acid which can dissolve or swell in the body.

FIG. 1 is a general view of the microneedle device 10. As shown in FIG. 1, a plurality of microneedles 1 for skin insertion are attached or integrally formed to the substrate 2.

The microneedles 1 for skin insertion are necessary to be penetrated into skin. Moreover, the tops of the microneedles 1 inserted into skin are essential to remain in skin with dissolution, swelling and breaking off in the skin. Thus, the microneedles 1 for skin insertion become gradually finer from the base to the top and are preferred to have sharp tops. In detail, the shape of the microneedles 1 is preferred to be circular cone or polygonal pyramid such as triangulate pyramid, quadrangular pyramid, hexagonal pyramid and octagonal pyramid.

The diameter or the length of one side to another at the base of the microneedles 1 for skin insertion is preferred to be 100 to 300 μm. The height of the microneedles 1 for skin insertion is preferred to be 100 to 1200 μm. The space between microneedles 1 is not specially defined and is preferred generally to be 100 to 1000 μm.

Pharmaceutical agents and cosmetic agents or at least one of them can be coated onto the surface of the microneedles 1 for skin insertion. However, water soluble pharmaceutical agents and cosmetic agents or at least one of them is preferred to be contained in the microneedles 1 for the purpose that make possible of the administration of a large quantity of pharmaceutical agents and cosmetic agents or at least one of them to the skin.

The pharmaceutical agent is not specially. As pharmaceutical agent, for example, there are antipyretic analgesic antiphlogistic agents, steroidal anti inflammatory drugs, vasodilator agents, antiarrhythmic agents, antihypertensive agents, local anesthetics, hormone agents, antihistaminics, general anesthetics, sedative hypnotics, antiepileptics, psychotherapeutic drugs, neuromuscular blocking agents, autonomic agents, antiparkinson agents, diuretics, vasoconstrictor agents, respiration stimulants, anesthetics.

As antipyretic analgesic antiphlogistic agents, for example, there are ibuprofen, flubiprofen, ketoprofen. As steroidal antiinflammatory drugs, for example, there are hydrocortisone, triamcinolone, prednisolone. As vasodilator agents, for example, there are diltiazem hydrochloride, isosorbide dinitrate. As antiarrhythmic agents, for example, there are procainamide hydrochloride, mexiletine hydrochloride.

As antihypertensive agents, for example, there are clonidine hydrochloride, bunitrolol hydrochloride, captopril. As local anesthetics, for example, there are tetracaine hydrochloride, propitocaine hydrochloride. As hormone agents, for example, there are propylthiouracil, estradiol, estriol, progesterone. As antihistaminics, for example, there are diphenhydramine hydrochloride, maleic acid chlorpheniramine.

As general anesthetics, for example, there are pentobarbital sodium. As sedative hypnotics, for example, there are amobarbital, phenobarbital. As antiepileptics, for example, there are phenytoin sodium. As psychotherapeutic drugs, for example, there are chlorpromazine hydrochloride, imipramine hydrochloride, chlordiazepoxide, diazepam. As neuromuscular blocking agents, for example, there are suxamethonium hydrochloride, eperisone hydrochloride.

As autonomic agents, for example, there are neostigmine bromide, bethanechol chloride. As antiparkinson agents, for example, there are amantadine hydrochloride. As diuretics, for example, there are hydroflumethiazide, isosorbide, fursemide. As vasoconstrictor agents, for example, there are phenylephrine hydrochloride. As respiration stimulants, for example, there are lobeline hydrochloride, dimorpholamine hydrochloride. As anesthetics, for example, there are morphine hydrochloride, cocaine hydrochloride, pethidine hydrochloride.

Soluble cosmetic agent is not specially defined, for example, it can be the one usually being used. As cosmetic agents, for example, there are whitening ingredients, antiwrinkle ingredients, blood circulation promotion ingredients, dietary aid, antibacterial agents, vitamins. As whitening ingredients, for example, there are ascorbic acid disodium phosphate, ascorbic acid glucoside, α(β)-arbutin, ascorbyl palmitate, kojic acid, resorcinol, tranexamic acid, licorice extract, retinoin. As antiwrinkle ingredients, for example, there are retinol, tretinoin, retinol acetate, vitamin A palmitate. As blood circulation promotion ingredients, for example, there are tocopheryl acetate, capsacin. As dietary aids, for example, there are raspberry ketone, evening primrose, seaweed extract. As antibacterial agents, for example, there are isopropylmethylphenol, photosensitizers, zinc oxide. As vitamins, for example, there are vitamin $D_2$, vitamin $D_3$, vitamin K.

Although either of the mentioned pharmaceutical agents has the molecular weight of less than 600, the one has high molecular weight also can be used. As preferable pharmaceutical agents that have high molecular weight, for example, there are bioactive peptide and its derivative, nucleinic acid, oligonucleotide, various kinds of antigens, bacteria, virus fragment.

As a bioactive peptide and its derivative, for example, there are calcitonin, adrenocorticotropic hormone, parathormone (PTH), hPTH (1→34), EGF, insulin, secretin, oxytocin, angiotensin, β-endorphin, glucagon, vasopressin, somatostatin, gastrin, luteinizing hormone-releasing hormone, enkephalin, neurotensin, atrial natriuretic peptide, somatotropin, somatotropin-releasing hormone, bradykinin, substance P, dynorphin, thyroid stimulating hormone, mammotrophic hormone, interferon, interleukin, G-CSF, glutathione peroxidase, superoxide dismutase, desmopressin, somatomedin, endothelin, placenta extract and salts of them. As antigens, for example, there are HBs surface antigen, HBe antigen, tetanus toxoid, diphtheria toxoid, amyloidβprotein.

As mentioned above, in the microneedle device 10, a plurality of microneedles 1 inserted into skin are fixed on the substrate 2. The substrate 2, which the microneedles 1 inserted into skin can be formed on, is not specially defined to have affinity of attachment with the microneedles 1 inserted into skin. The substrate 2 can be a film or sheet made of materials such urethane resin, polyvinyl alcohol and aluminum. The thickness of the substrate 2 can be, for example, 100 to 1000 μm. In addition, the substrate 2 can be fabricated of materials that can dissolve or swell in the body like the microneedles 1 inserted into skin.

The method of manufacturing of the microneedle device 10 is not specially limited. The microneedle device 10 can be fabricated by any well-known method, such as the following method (1) to (4).

In the method (1), the solution which contains over 50 weight percent of biomaterials chosen from chitosan, collagen, gelatin, hyaluronic acid as solute that can dissolve or swell in the body, and if necessary, the pharmaceutical agents and cosmetic agents or at least one of them, is put on the mold in which the holes corresponding to the microneedle shapes 1 have been patterned. Then dry the solution at room temperature or by heating to evaporate water. After laminating the substrate 2 to the needles, the microneedles 1 for skin insertion and substrate 2 are obtained by peeling them off from the mold.

In the method (2), the solution described above is put on the mold mentioned above to form a substrate layer on the mold and microneedles in the mold. After evaporating the water of the solution at room temperature or by heating, the microneedle device is obtained by peeling the substrate off from the mold.

According to the method (2), can be obtained the microneedle device 10, of which the substrate 2 and the microneedles 1 for skin insertion are both fabricated. The above microneedles contain over 50 weight percent of biomaterials chosen from chitosan, collagen, gelatin, hyaluronic acid which can dissolve or swell in the body, and can contain pharmaceutical agents and cosmetic agents or at least one of them according to the requirement.

In the method (3), the solution which contains over 50 weight percent of biomaterials chosen from chitosan, collagen, gelatin, hyaluronic acid, materials that can dissolve or swell in the body, and pharmaceutical agents and cosmetic agents or at least one of them according to the requirement; is injected as the microneedles 1 for skin insertion onto the substrate 2. And then the microneedle device is obtained by drying the solution at room temperature or by heating.

In the method (4), as shown in FIG. 2, the film substrate 5 is formed by drying the solution at room temperature or by heating. The solution contains over 50 weight percent of biomaterials chosen from chitosan, collagen, gelatin, hyaluronic acid, other materials that can dissolve or swell in the body, and pharmaceutical agents and cosmetic agents dr at least one of them according to the requirement. The V-shaped part 4 is formed by cutting the shape of V notch on the film substrate 5. The microneedle device is obtained by folding up the V-shaped part 4 as shown in arrow 6 in FIG. 2 to form the microneedles 3 for skin insertion In the mentioned methods of manufacturing, as a material of the microneedles 1 for skin insertion, the needles can be composed of over 50 weight percent of the biomaterials chosen from chitosan, collagen, gelatin, and other materials those can dissolve or swell in the body. It is preferred to use collagen from biological origin with 50 to 70 weight percent and hyaluronic acid from biological origin with 50 to 30 weight percent and other biomaterials dissolve or swell in the body.

The composition of the microneedle device 10 is as mentioned above. The microneedles 1 for skin insertion of the microneedle device 10 have suitable mechanical strength, toughness and hardness, and can be easily inserted into skin without breaking followed by dissolving and disappearing in the skin.

Therefore, it is possible to actually deliver the biomaterials chosen from chitosan, collagen, gelatin or hyaluronic acid to the desired part of skin. It is also possible to deliver pharmaceutical agents and cosmetic agents or at least one of them to the desired part of skin by adding them in the microneedles 1 for skin insertion. In addition, the microneedles 1 for skin insertion are able to contain a great quantity of pharmaceutical agents and cosmetic agents if pharmaceutical agents and cosmetic agents are water soluble. Moreover, it is not necessary to fabricate the microneedle device by heating when soluble biomaterials are used as the material of the microneedles for skin insertion. In this way, the decrease in the effect of pharmaceutical agents and cosmetic agents due to heat decomposition can be avoided.

The present invention is explained by the following examples but it is not limited in the following examples.

Example 1

The collagen solution was obtained by dissolving of 20 weight parts of collagen (Nippi Corporation, Trade name [Rias Shark], molecular weight of 5000) in 100 weight parts of water at room temperature. The resulting solution was put on the polymethylmethacrylate sheet, and the collagen substrate of 500 μm in thickness was obtained with drying at room temperature. A great deal of the V-shaped notch were formed by cutting the shape of V on the resulting collagen substrate as shown in FIG. 2. A plurality of the microneedles for skin insertion of 800 μm in height and 300 μm in width of the base were formed by folding the V-shaped parts. When the resulting microneedle device was pressed onto the facial skin of a subject, a plurality of pores was formed on the facial skin of the subject without pain. After removing the microneedle device, solution containing 1 weight percent of ascorbic acid disodium phosphate was applied on the pores formed skin skte. It was shown that vitamin C that could be easily decomposes easily on heating permeated safely into skin in the above way.

Example 2

The sodium hyaluronate solution was obtained by dissolving 15 weight parts of sodium hyaluronate (Kibun Food Chemical Co., trade name FCU-SU, obtained with the cultivation, molecular weight of 100000) and 0.15 weight parts of ascorbic acid disodium phosphate in the 100 weight parts of water at room temperature. The microneedle device was produced using the resulting solution according to the method described in the example 1. The resulting microneedle device was 1 cm in diameter, and was set on the round tape of 2 cm in diameter. The microneedle device was pressed onto the freckle site of facial skin of a subject treeing the microneedles reach the site of 200 μm in depth and was removed after an hour. It was evident that a plurality of break off tips of microneedles inserted into skin were left in the facial skin of the subject without pain. After continuous application of the above described microneedle device for one month, the freckle on the facial skin of the subject became thinner.

Example 3

The collagen solution was obtained by dissolving 20 weight parts of collagen (Nippi Corporation, Trade name [Rias Shark], molecular weight of 5000) and 0.06 weight parts of a-arbutin (Esaki Guliko Co.) in 100 weight parts of water at room temperature. The microneedle device was produced using the resulting solution following the Example 1. The resulting microneedle device was set on the round tape of 2 cm in diameter. The microneedle device was pressed onto the freckle site of facial skin of a subject making the microneedles inserted into skin of 200 μm in depth and was removed after an hour. It was evident that a plurality of break off tips of microneedles inserted into skin is left in the facial skin of subject without pain.

Example 4

The sodium hyaluronate solution was obtained by dissolving 20 weight parts of sodium hyaluronate (Kibun Food Chemical Co., trade name FCU-SU, obtained with the cultivation, molecular weight of 100000) 0.2 weight parts of Tartorazine (Nakalai tesque Co., orange pigment, model compound) in 100 weight parts of water at room temperature. The resulting solution was put on the mold on which cone-shaped holes of 600 μm in depth and 200 μm in diameter of the base had patterned. After drying at room temperature, the microneedle device as shown in FIG. 1 was obtained by peeling off the device from the mold. The microneedles for skin insertion formed in the resulting microneedle device were cone-shaped of 600 μm in depth and 200 μm in diameter at the base. The area of the substrate was 1 cm². The resulting device together with the adhesive tape of 2 cm in diameter were pressed on the rat skin and removed after an hour. After daily application of needles device for one month, it was evident that tartorazine permeated deeply into skin by the observation of the cross section of rat skin using microscope.

Example 5

The sodium hyaluronate solution was obtained by dissolving 20 weight parts of sodium hyaluronate (Kibun Food Chemical Co., trade name FCU-SU, obtained with the cultivation, molecular weight of 100000) and 0.2 weight parts of coomassie brilliant blue (TokyoKasei Co., blue pigment, model compound) in 100 weight parts of water at room temperature. The microneedle device was produced using the above described solution following Example 4. The microneedles for skin insertion formed on the resulting microneedle device were cone-shaped of 600 μm in depth and 200 μm in base diameter. The resulting microneedle device was set on the round adhesive tape of 2 cm in diameter, and was pressed on the rat skin together with the adhesive tape and removed after an hour. With the observation of the cross section of rat skin, it was evident that in the skin, the skin was stained with coomassie brilliant blue at the site of microneedle insertion.

Example 6

The chitosan solution was obtained by dissolving 10 weight parts of chitosan (SE Chemical Co., trade name [Chitosan S E C F 3]) in the mixed solution of 50 weight parts of water and 50 weight parts of methanol at room temperature. The microneedle device was produced using the above described solution following Example 4. The microneedles for skin insertion formed on the resulting microneedle device were cone-shaped of 600 μm in depth and 200 μm in base diameter. When the resulting microneedle device was pressed onto the facial skin of a subject, a plurality of pores was formed on the facial skin of the subject without pain. And then the solution containing 1 weight percent of hydroquinone was applied on the pore sites of skin. It became evident that hydroquinone permeated into skin.

Example 7

The collagen-hyaluronate acid mixed solution was obtained by dissolving 14 weight parts of collagen (Nippi Corporation, trade name [RiasShark], molecular weight of 5000) and the 7 weight parts of sodium hyaluronate (Kibun Food Chemical Co., trade name FCU-SU, obtained with the cultivation, molecular weight of 100000) in 100 weight parts of water. The microneedle device was produced using the above solution following Example 4. The resulting microneedle device was set on the round adhesive tape of 2 cm in diameter, pressed onto the wrinkles on the forehead of a subject together with the tape and removed after an hour. Just after application, the site of wrinkles bulged and became ambiguous. This effect lasted about two months after application.

Example 8

The sodium hyaluronate-all-trans retinol solution was obtained by dissolving 14 weight parts of sodium hyaluronate (Kibun Food Chemical Co., trade name FCH-80, obtained with the cultivation, molecular weight of 800000) and 0.056 weight parts of all-trans retinal (Nakalai tesque Co., reagent) in 100 weight parts of water. The resulting solution was put on the same mold as that used in Example 4 and was concentrated to evaporate water at room temperature for 30 minutes. Then the concentrated solution on the surface of the mold was wiped out with gauzes remaining the solution filled in cone-shaped holes. The solution that contained only hyaluronate acid prepared by dissolving 20 weight parts of sodium hyaluronate in 100 weight parts of water, was put on the mold to make the solution layer of 1 mm in thickness. After drying for 24 hours in atmosphere, the microneedle device, of which all-trans retinal was only contained in the microneedles, was obtained by peeling off the device off the mold. The shape of the microneedle device was round with the area of 1 cm². The microneedles were inserted by pressing the resulting microneedle device onto the maculae on the facial skin of a subject and removed after an hour. The microneedle device was applied with the same procedure three times a day. One week later, the maculae almost disappeared.

Example 9

The gelatin solution was prepared by dissolving 15 weight parts of gelatin (Nippi Corporation, trade name [Nippi Highgrade gelatin A P A T], molecular weight of 60000) in 100 weight parts of water. The microneedle device was produced using the above solution following Example 4. The resulting microneedle device was fixed on the round adhesive tape of 2 cm in diameter, pressed onto the wrinkle on the forehead of a subject together with the adhesive tape and removed after an hour. Just after application, the site of wrinkle bulged and became ambiguous. This effect lasted about two months after application.

Example 10

The gelatin-hyaluronate acid mixed solution was prepared by dissolving 0.15 g gelatin (NippiCorporation, trade name [Nippi Highgrade gelatin A P A T ], molecular weight of 60000) and 0.05 g sodium hyaluronate (Kibun Food Chemical Co., trade name FCH-80, obtained with the cultivation, molecular weight of 800000) in 1 g water. The bovine insulin solution (0.003 g/ml) was obtained by dissolving bovine insulin (Nakalai tesque Co.) in pH 2.5 hydrochloric acid solution. The insulin solution was prepared by adding 1 ml bovine insulin solution into the gelatin-hyaluronate acid mixed solution. The microneedle device (insulin microneedles) was obtained using the resulting insulin solution following Example 4. The resulting microneedle device was set on the round adhesive tape of 2 cm in diameter and was used in the following insulin delivery experiment together with the adhesive tape.

The Induction of Diabetic Rats

STZ (streptozotocin) solution was prepared by dissolving in the citric acid buffer solution (pH 4.4). Diabetes was induced by rat tail vein injection of 50 mg/kg STZ solution. The plasma glucose levels of the rats were determined after the second and third week, and the rats with the fasting plasma glucose levels exceeded 250 mg/dl were selected to be used in the following insulin delivery experiment.

Insulin Delivery Experiment

The diabetic rats were fasted for 14 hours before the experiment. After the rats were anesthetized with Nembutal (30 mg/kg), the abdominal region was carefully shaved. Then the microneedle device was applied onto the abdominal skin by punching from the back of the tape and was used for an hour. At 3, 5, 7 and 9 h after the application, blood samples were collected from rats and the plasma glucose levels were determined. The result was shown in table 1.

TABLE 1

| | The percentage in plasma glucose level (the plasma glucose level at each time point/the initial level) × 100 | | | | |
|---|---|---|---|---|---|
| | 0 | 3 h | 5 h | 7 h | 9 h |
| Example 10 | 100 | 56 | 47 | 34 | 32 |

(Comparison 1)

The maltose monohydrate solution obtained by dissolving 50 weight parts of maltose monohydrate (Nakalai tesque Co.) in 100 weight parts of water, was put on the mold used in the example 4 and dried under reduced pressure at 36° C. for 24 hours. After the drying, the microneedle device was reinforced from the back with adhesive tape and then peeled off from the mold. When the microneedle device was used to insert into skin after 10 minutes at room temperature, the tops of microneedles for skin insertion became soft due to the atmosphere moisture. Thus, it was unable to insert them into skin.

(Comparison 2)

The maltose sheet was prepared by the same procedure as Example 1 using the maltose monohydrate solution obtained from comparison 1. When the shape of V was cut on the resulting maltose sheet to form the V-shaped part, it was unable to form V-shaped part by folding.

FEASIBILITY OF UTILIZATION IN THE INDUSTRIALIZATION

The microneedle device of the present invention can be used in the field of pharmaceutic, cosmetic.

What is claimed is:

1. A microneedle device comprising:
   a substrate, and
   cone-shaped or pyramid-shaped microneedles for skin insertion on the substrate, the above mentioned microneedles for skin insertion being fabricated from materials that can dissolve or swell in the body and that contain over 50 weight percent of one or multiple biomaterials chosen from chitosan, collagen, gelatin, and hyaluronic acid,
   wherein the mentioned microneedles for skin insertion are characterized by containing 50 to 70 weight percent of collagen and 50 to 30 weight percent of hyaluronic acid.

2. The microneedle device of claim 1, wherein the mentioned microneedles for skin insertion are characterized by also containing pharmaceutical agents and cosmetic agents or at least one of them.

3. The microneedle device of claim 1, wherein the mentioned substrate is characterized in that it is made of a material that can dissolve or swell in the body and includes the V-shaped part formed by cutting V notch, the mentioned microneedles for skin insertion are characterized by being formed by folding the mentioned V notch part to be a needle.

4. A method of manufacturing the microneedle device of claim 1, the microneedle device comprising: a substrate, and cone-shaped or pyramid-shaped microneedles for skin insertion on the substrate, the above mentioned microneedles for skin insertion being fabricated from materials that can dissolve or swell in the body and that contain over 50 weight percent of one or multiple biomaterials chosen from chitosan, collagen, gelatin, and hyaluronic acid, wherein the mentioned microneedles for skin insertion are characterized by containing 50 to 70 weight percent of collagen and 50 to 30 weight percent of hyaluronic acid, and wherein the mentioned microneedles for skin insertion are characterized in that they are fabricated by forming the V-shaped part by cutting V notch on the substrate made of a material that can dissolve or swell in the body and folding the mentioned V-notch part to be a needle.

* * * * *